(12) United States Patent
Nevo

(10) Patent No.: US 6,516,213 B1
(45) Date of Patent: Feb. 4, 2003

(54) METHOD AND APPARATUS TO ESTIMATE LOCATION AND ORIENTATION OF OBJECTS DURING MAGNETIC RESONANCE IMAGING

(75) Inventor: Erez Nevo, Natania (IL)

(73) Assignee: Robin Medical, Inc., Baltimore, MD (US)

(*) Notice: Subject to any disclaimer, the term of this patent is extended or adjusted under 35 U.S.C. 154(b) by 0 days.

(21) Appl. No.: 09/762,953
(22) PCT Filed: Sep. 3, 1999
(86) PCT No.: PCT/US99/20216
§ 371 (c)(1), (2), (4) Date: Feb. 15, 2001
(87) PCT Pub. No.: WO00/13586
PCT Pub. Date: Mar. 16, 2000

(51) Int. Cl.[7] .................................. A61B 5/05
(52) U.S. Cl. ........................ 600/424; 600/410
(58) Field of Search ................. 600/424, 410, 600/407, 411; 128/899; 324/207.13, 207.22, 260, 207.17, 326

(56) References Cited

U.S. PATENT DOCUMENTS 5,307,808 A * 5/1994 Dumoulin et al. ....... 128/653.2
5,425,367 A * 6/1995 Shapiro et al. ............ 128/653.1
5,558,091 A * 9/1996 Acker et al. ................ 600/424
5,913,820 A * 6/1999 Bladen et al. .............. 600/407
6,016,439 A * 1/2000 Acker ........................ 600/411

* cited by examiner

Primary Examiner—Teresa Walberg
Assistant Examiner—Quang Van

(57) ABSTRACT

Method and apparatus for determining the instantaneous location, the orientation of an object moving through a three-dimensional space by applying to the object a coil assembly including a plurality of sensor coils (20) having axes of known orientation with respect to each other including components in the three orthogonal planes; generating a time-varying, three-dimensional magnetic field gradient having known instantaneous values of magnitude and direction; applying the magnetic field gradient to the space, and object moving therethrough to induce electrical potentials in the sensor coils; measuring the instantaneous values of the induced electrical potentials generated in the sensor coils; processing the measured instantaneous values generated in the sensor coils together with the known magnitude, direction of the generated magnetic field gradient, the known relative orientation of the sensor coils in the coil assembly to compute the instantaneous location, orientation of the object within the space.

36 Claims, 7 Drawing Sheets

METHOD AND APPARATUS TO ESTIMATE LOCATION AND ORIENTATION OF OBJECTS DURING MAGNETIC RESONANCE IMAGING

FIELD OF THE INVENTION

The invention relates to methodology and apparatus to determine the location and orientation of an object, for example a medical device, located inside or outside a body, while the body is being scanned by magnetic resonance imaging (MRI). More specifically, the invention enables estimation of the location and orientation of various devices (e.g. catheters, surgery instruments, biopsy needles, etc.) by measuring voltages induced by time-variable magnetic fields in a set of miniature coils. Such time-variable magnetic fields are generated by an MRI scanner during its normal operation.

BACKGROUND OF THE INVENTION

Minimally invasive procedures: Minimally-invasive diagnostic or interventional procedures require either direct visual viewing or indirect imaging of the field of operation and determination of the location and orientation of the operational device. For example, laparoscopic interventions are controlled by direct viewing of the operational field with rigid endoscopes, while flexible endoscopes are commonly used for diagnostic and interventional procedures within the gastrointestinal tract. Vascular catheters are manipulated and manoeuvred by the operator, with real-time X-ray imaging to present the catheter location and orientation. Ultrasound imaging and new real-time MRI and CT scanners are used to guide diagnostic procedures (e.g. aspiration and biopsy) and therapeutic interventions (e.g. ablation, local drug delivery) with deep targets. While the previous examples provide either direct (optical) or indirect (imaging) view of the operation field and the device, another approach is based on remote sensing of the device with mechanical, optical or electromagnetic means to determine the location and orientation of the device inside the body.

Stereotaxis: Computer-assisted sterotaxis is a valuable technique for performing diagnostic and interventional procedures, most typically with the brain. The concept behind the technique is to have real-time measurement of the device location in the same coordinate system as an image of the field of operation. The current location of the device and its future path are presented in real-time on the image and provide the operator with feed-back to manipulate the device with minimal damage to the organs. During traditional sterotaxis, the patient wears a special halo-like headframe, which provides the common coordinate system, and CT or MRI scans are performed to create a three-dimensional computer image that provides the exact location of the target (e.g. tumour) in relation to the headframe. The device is mechanically attached to the frame and sensors provide its location in relation to the head frame. When this technique is used for biopsy or minimally-invasive surgery of the brain, it guides the surgeon in determining where to make a small hole in the skull to reach the target. Newer technology is the frameless technique, using a navigational wand without the headframe (e.g. Nitin Patel and David Sandeman, "A Simple Trajectory Guidance Device that Assists Freehand and Interactive Image Guided Biopsy of Small Deep Intracranial Targets", Comp Aid Surg 2:186–192, 1997). In this technique remote sensing system (e.g. light sources and sensors) provides the real-time location of the device with respect to the image coordinate system. Yet both the sterotaxis and the frameless techniques are typically limited to the use of rigid devices like needles or biopsy forceps since their adequate operation requires either mechanical attachments or line of sight between the light sources and the sensors.

Electromagnetic remote sensing: Newer remote sensing techniques are based on electromagnetism. For example, Acker et al (U.S. Pat. No. 5,558,091) disclose such a method and apparatus to determine the position and orientation of a device inside the body. This method uses magnetic fields generated by Helmholtz coils, and a set of orthogonal sensors to measure components of these fields and to determine the position and orientation from these measurements. The measurement of the magnetic field components is based on Hall effect and requires exciting currents in the sensors in order to generate the measured signals. The technique requires control of the external magnetic fields and either steady-state or oscillating fields, for the induced voltages to reach a state of equilibrium. These requirements prevent, or greatly complicate, the use of this technique with magnetic fields generated by the MRI system, and requires the addition of a dedicated set of coils to generate the required magnetic fields.

A different approach for remote sensing of location is disclosed by Pfeiler et al. (U.S. Pat. No. 5,042,486) and is further used by Ben-Haim for intra-body mapping (U.S. Pat. No. 5,391,199). Their technology is based on generating weak radio-frequency (RF) signals from three different transmitters, receiving the signals through an RF antenna inside the device, and calculating the distances from the transmitters, which define the spatial location of the device. As with the previous methodology, the application of the technology to MRI is problematic due to the simultaneous use of RF signals by the MR scanning. Potential difficulties are the heating of the receiving antenna in the device by the high amplitude excitation RF transmissions of the MRI scanner and artifacts in the MR image.

Dumoulin and colleagues disclose another approach to determine the location of a device, using a small receiving coil which is sensitive to near-neighbourhood emitted RF signal during the MR imaging process (Dumoulin C L, Darro R D, Souza S P, "Magnetic resonance tracking", in Interventional MR, edited by Jolesz F A and Young I Y, Mosby, 1998). This method cannot directly determine the orientation of the device, and may be subject to similar difficulties as the previous technology, including heating of the coil.

Interventional MRI: Many of the advantages of MRI that make it a powerful clinical imaging tool are also valuable during interventional procedures. The lack of ionizing radiation and the oblique and multi-planar imaging capabilities are particularly useful during invasive procedures. The absence of beam-hardening artifacts from bone allows complex approaches to anatomic regions that may be difficult or impossible with other imaging techniques such as conventional CT. Perhaps the greatest advantage of MRI is the superior soft-tissue contrast resolution, which allows early and sensitive detection of tissue changes during interventional procedures. Many experts now consider MRI to be one of the most powerful imaging techniques to guide interventional interstitial procedures, and in some cases even endovascular or endoluminal procedures (Yoshimi Anzai, Rex Hamilton, Shantanu Sinha, Antonio DeSalles, Keith Black, Robert Lufkin, "Interventional MRI for Head and Neck Cancer and Other Applications", Advances in Oncology, May 1995, Vol 11 No. 2).

From the present background on current methodologies, one can define the ideal system for minimal invasive procedures: It should provide real-time, 3-dimensional, non-ionizing imaging (like MRI or ultrasound) as feed-back to the user for optimal insertion and intervention; it should implement flexible, miniaturized devices which are remotely sensed to provide their location and orientation. By combining a composite image of the field of operation and the device location and orientation, the operator can navigate and manipulate the device without direct vision of the field of operation and the device. This may facilitate the use of minimal invasive intervention in the brain or other organs.

OBJECTS AND SUMMARY OF THE INVENTION

An object of the present invention is to provide a novel method and apparatus for determining the instantaneous location and orientation of an object moving through a three-dimensional space, which method and apparatus have advantages in one or more of the above respects.

Another object of the present invention is to provide such a method and apparatus which is particularly useful in MRI systems by making use of a basic universal component of the MRI system, namely the time-varying magnetic gradients which are typically generated by a set of three orthogonal electromagnetic coils in such systems.

According to one aspect of the present invention, there is provided a method of determining the instantaneous location and orientation of an object moving through a three-dimensional space, comprising: applying to the object a coil assembly including a plurality of sensor coils having axes of known orientation with respect to each other and including components in the three orthogonal planes; generating a time-varying, three-dimensional magnetic field gradient having known instantaneous values of magnitude and direction; applying the magnetic field gradient to the space and the object moving therethrough to induce electrical potentials in the sensor coils; measuring the instantaneous values of the induced electrical potentials generated in the sensor coils; and processing the measured instantaneous values generated in the sensor coils, together with the known magnitude and direction of the generated magnetic field gradient and the known relative orientation of the sensor coils in the coil assembly, to compute the instantaneous location and orientation of the object within the space.

The above-described method is particularly useful in MRI systems, wherein the magnetic field gradient is generated by activating the gradient coils of an MRI scanner, and the invention is therefore described below with respect to such a system.

According to further features in the described preferred embodiment, the magnetic field gradient is generated by activating three orthogonally disposed pairs of gradient coils according to a predetermined activating pattern; and the measured instantaneous values of the induced electrical potentials generated in the sensor coils are processed, together with the predetermined activating pattern of the gradient coils and the known relative orientation of the sensor coils, to provide an estimate of the location and orientation of the object.

According to another aspect of the present invention, there is provided apparatus for determining the instantaneous location and orientation of an object moving through a three-dimensional space, comprising: a coil assembly carried by the object and including a plurality of sensor coils having axes of known orientation with respect to each other and including components in the three orthogonal planes; a magnetic field generator generating for a time-varying, three-dimensional magnetic field gradient having known instantaneous values of magnitude and direction in the space and the object moving therethrough to induce electrical potentials in the sensor coils; means for measuring the instantaneous values of the induced electrical potentials generated in the sensor coils; and a processor for processing the measured instantaneous values generated in the sensor coils, together with the known magnitude and direction of the generated magnetic field gradient and the known relative orientation of the sensor coils in the coil assembly, to compute the instantaneous location and orientation of said object within said space.

The disclosed methodology and apparatus enable the estimation of the location and orientation of an object or a device by using a set of miniature, preferably (but not necessarily) orthogonal coils. The simplest, preferred embodiment has a set of three orthogonal coils. However more complex coil sets, for example a set of three orthogonal pairs of parallel coils, can improve the accuracy of the tracking with a higher cost of the system. To simplify the presentation, the following disclosure deals specifically with a set of three orthogonal coils, and also refers to the more complex configuration of three orthogonal pairs of coils. However the same concepts can be applied to various combinations of coils by anyone familiar with the field of the invention.

The time change of magnetic flux through a coil induces electromotive force (i.e. electric potential) across the coil (Faraday Law of electromagnetism). MRI scanners generate time-variable magnetic fields to create magnetic gradients in the scanned volume. By measuring the induced electric potentials in the three orthogonal coils (or pairs of coils), and by getting the time pattern of the generated magnetic gradients as input from the MRI scanner, both the location and orientation of the device can be estimated.

The present invention has significant advantages over existing methodologies. Compared with sterotaxis, either the frame or frameless techniques, the new methodology enables the use of devices like catheters or surgical instrumentation without the need for direct line of sight with the device. Unlike the remote electromagnetic localization methodology of Acker et al the present invention is based on measurement of voltages induced by a set of time-varying electromagnetic gradient fields in a set of coils (Faraday Law), rather than the need to use homogenous and gradient fields which induce voltages in a set of miniature conductors carrying electrical current (Hall effect). Thus, the present invention is totally passive, it does not require any excitation of the sensors, nor the use of dedicated magnetic fields, and the requirement for time-variable magnetic fields is satisfied with virtually any MRI scanning protocol which is in routing clinical use. The methods disclosed by Pfeiler et al and Dumouline et al require the use of two sensors to measure orientations and thus have limited accuracy of orientation estimation, while the present invention uses a sensor which provides simultaneously accurate orientation and location tracking. Unlike existing optical tracking systems, there is no limitation on the number of sensors being used, and there is no need to maintain a line of sight between the sensor and the tracking apparatus. All other tracking methodologies are based on their own reference system, and should be aligned with the MRI coordinate system by a time-consuming registration procedure. The disclosed tracking methodology does not require registration since it uses the same set of gradient coils which are used by the MRI scanner for spatial encoding of the images.

BRIEF DESCRIPTION OF THE DRAWINGS

FIG. 5A shows a cubic configuration for extra-corporeal applications with three orthogonal coils having a typical size of up to 10 mm. FIG. 5B shows a cubic configurations with 3 orthogonal pairs of parallel coils. FIGS. 5C–5D show a cylindrical configuration for use with catheters with a typical diameter of 2–3 mm. FIG. 5C illustrates an axial (along the K axis) view, while FIG. 5D shows a 3-dimensional display of the sensor, having one cylindrical coil (22) and two pairs of transverse "saddle" coils (24, 26).

DETAILED DESCRIPTION OF THE PREFERRED EMBODIMENT

Figure 1A:
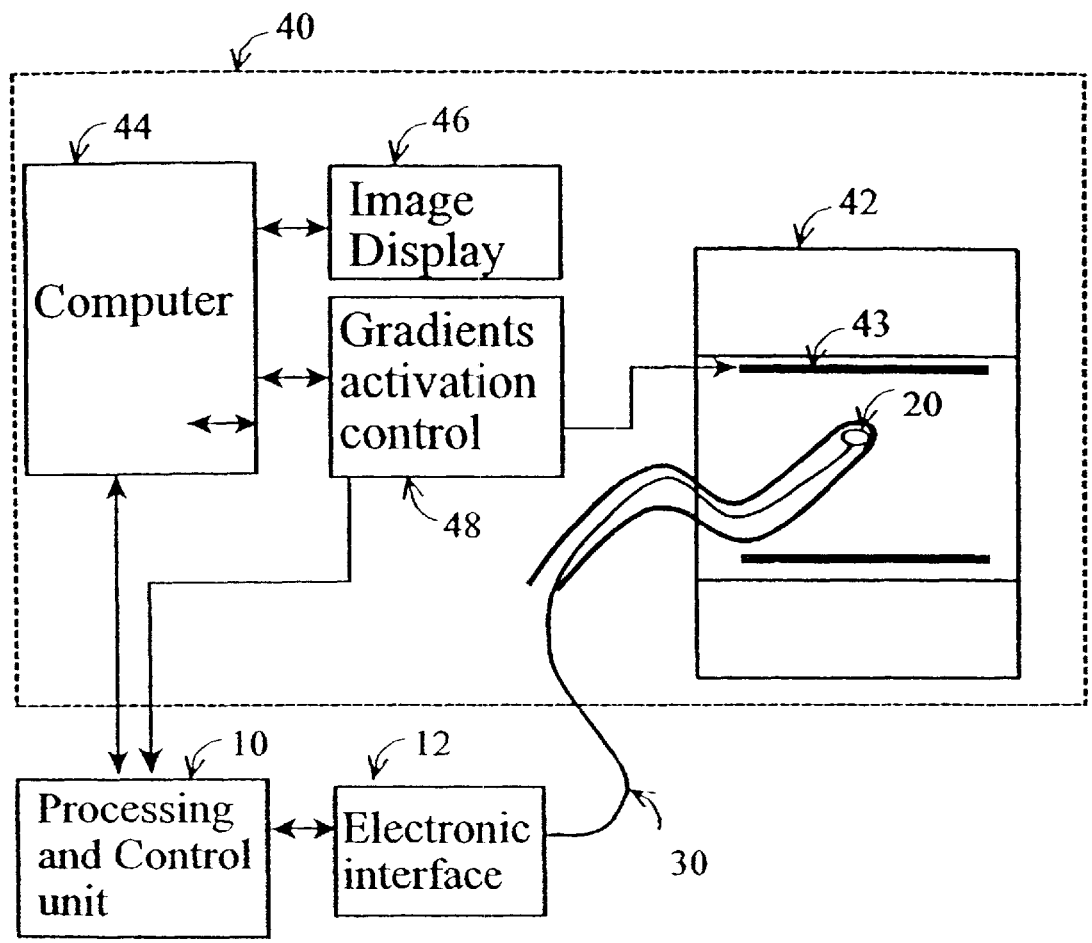
FIG. 1A provides a block diagram description of the invented apparatus which includes a processing and control unit (10), a sensor (20), the module is integrated into or attached to an object or a device (30), electronic interface (12), and MRI system (40) with its main coil (42), three gradient coils (43), computer (44), gradient coils control unit (48), and image display (46). The MRI coils (42 and 43) are presented in more details in FIG. 1B with the different coils displaced along the MRI main axis to clarify the presentation.
Figure 1B:
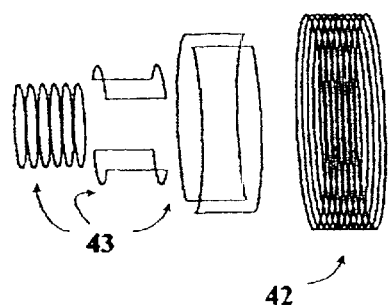

Referring now to FIG. 1, a typical MRI system (40) has several modules which are specifically relevant to the current invention: the three gradient coils (43), the gradient coils control unit (48), and the image display (46). The exact implementation of the invented methodology depends on the MRI mode of imaging, and the following presentation relates, as a typical example, to a standard MRI spin-echo imaging mode. During the spin-echo protocol, repeated generation of magnetic fields by the 3 gradient coils provide the spatial encoding of the received MR echo and enable the reconstruction of the image. A sample sequence is given in FIG. 2 (recorded from a Signa MRI system, General Electric, USA). For this sequence the system activates the Z-gradient coil for "slice selection", simultaneously the X and Y gradient coils for "phase encoding" and the X gradient coil for the "read out" phase.

Figure 2:
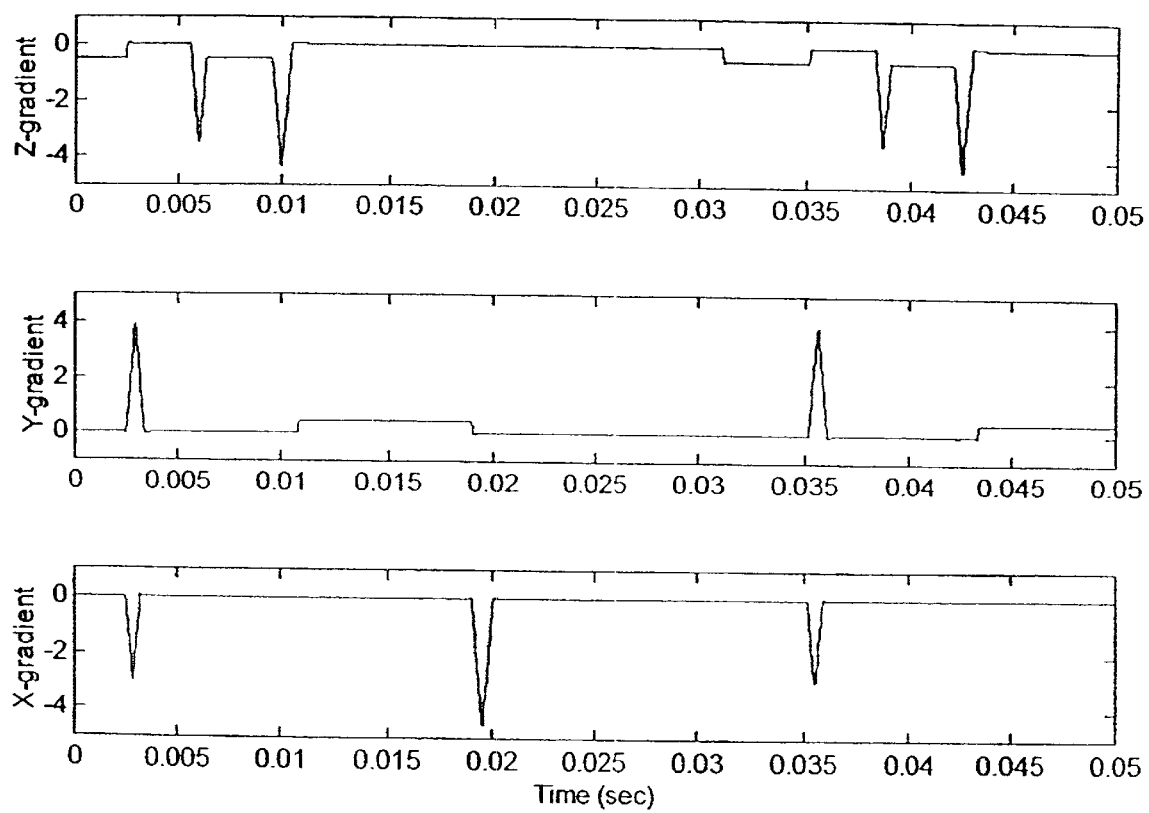
FIG. 2 presents the activation sequence of the MRI gradient coils as functions of time during a standard spin echo scan. The step rise and drop of the generated magnetic fields result with high rate of change of the magnetic flux through the coils.

The gradient control unit (48) provides the processing unit (10) with real-time presentation of the activation sequence of the three gradient coils which generate the magnetic gradients (FIG. 2). The magnetic fields which are generated by the gradient coils have components in all three axes (X, Y, Z), but each of the coils has a precise linear change of the amplitude of the Z-component along one axis only, where these coils and the generated magnetic gradients are termed by this specific axis (i.e. for the Z-gradient (Gz) the Z-component varies linearly with the Z-coordinate, for the X-gradient (Gx) the Z-component varies linearly with the X-coordinate, and for the Y-gradient (Gy) the Z-component varies linearly with the Y-coordinate). The other components of the magnetic fields of the gradient coils have a specific spatial distribution which depends on the specific design of the gradient coils. A full description of the magnetic field as function of time and location with any mode of operation (G(t,x,y,z)) can be calculated within the processing unit (10) by vectorial summation of the three time-variable magnetic fields of the gradient coils and the time-invariant main field (Bo) of the MRI scanner (in the following presentation vectors are underlined, to distinguish from scalars):

(1) $\underline{G}(t,x,y,z)=\underline{Gx}(t,x,y,z)+\underline{Gy}(t,x,y,z)+\underline{Gz}(t,x,y,z)+\underline{Bo}(x,y,z)$ where x,y,z are coordinates along the three axes of the MRI coordinate system (X, Y, Z, respectively) and t is a time variable. Additional magnetic fields, which are generated by the RF (radio frequency) coils of the MRI, are not being used by the current invention. These fields, which alternate in the range of mega-hertz, induce high-frequency electrical potentials in the sensing coils which can be removed by low-pass filtration.

In one preferred embodiment (FIG. 4A), the sensor (20) consists of a set of three orthogonal sensing coils (22, 24, 26). The time varying magnetic field $\underline{Gx}(t,x,y,z)$ induces electric potential, or voltage (V), in each of the sensing coils, and the magnitude of the induced voltage is related to the time-derivative of the magnetic flux Θ through the coil, as given by Faraday Law:

(2) $V=-d\Theta/dt$ the magnetic flux at each location is determined by the magnetic field $\underline{G}(t,x,y,z)$, the coil area (A), and the direction of the magnetic field with respect to the spatial orientation of the coil, as defined by a unit vector $\underline{n}$ vertical to the plane of the coil:

(3) $\Theta=\underline{G}(t)\cdot\underline{n}A$ where the dot denotes a vectorial dot product.

Combining equations 1–3, the induced voltages in the coils are directly related to the time derivative of the magnetic field:

(4) $V=-d[(\underline{Gx}(t,x,y,z)+\underline{Gy}(t,x,y,z)+\underline{Gz}(t,x,y,z)+\underline{Bo}(x,y,z))\cdot\underline{n}A]/dt$ If the sensor does not move or rotate, the Bo field and the direction vector $\underline{n}$ are constant and the induced voltage in each coil is given by:

(5) $V=-d[(\underline{Gx}(t,x,y,z)+\underline{Gy}(t,x,y,z)+\underline{Gz}(t,x,y,z))]/dt\cdot\underline{n}A$ The measured magnitudes of the induced voltages at the three coils and the known magnetic field $\underline{G}(t,x,y,z)$ as function of time at each point in the operating field (as calculated by summing the individual magnetic fields of all gradient coils which are active at a specific time) enable the estimation of the object location and direction by the following sequence of steps. This sequence of steps is only one option out of several possible approaches which are similar in concept and only differ in the actual embodiment of the estimation process.

Step 1. Measurement of induced voltages

The induced voltages in the three-orthogonal coils (FIG. 4) enable the calculation of the magnetic fields of the gradient coils at the location of the sensor without knowing the orientation of the sensor. While the magnitudes of the induced voltages at each coil change with the orientation, their vectorial sum is independent of the orientation and is proportional to the time-derivative of the magnetic field at the location of the sensor, as given by equations 4 and 5. For example, during activation of the Z-gradient, the time-varying magnetic field induces three voltages in the three coils. For a configuration with three orthogonal pairs of parallel coils (FIG. 5B), the induced voltages in two parallel coils of each pair are averaged and the results are analyzed similarly as with three single coils.

Figure 4A:
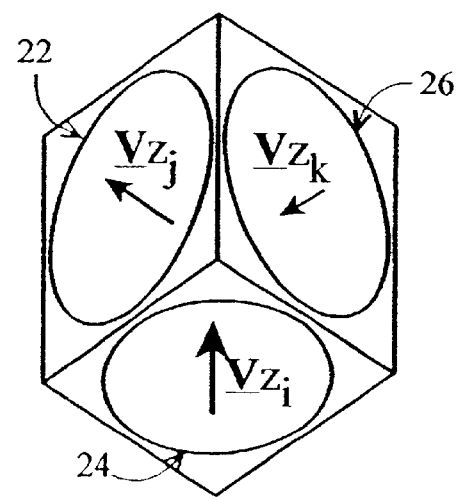
FIG. 4A provides a schematic configuration of three-orthogonal coils (22, 24, 26) in the sensor (20) and the induced voltages in each coil.
Figure 4B:
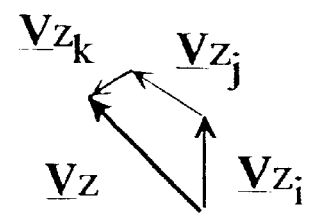
FIG. 4B presents an example of the vectorial summation of the voltages induced in each coil during activation of the magnetic field of the Z-gradient coil into a voltage vector termed $\underline{Vz}$.

Thus during activation of the Z-gradient the three voltages $Vz_i$, $Vz_j$, $Vz_k$ correspond either to the measured voltages in the three single coils or are the averages of the measured voltages in each of the three pairs of coils. We define the induced voltages as vectors $\underline{Vz_i}$, $\underline{Vz_j}$, $\underline{Vz_k}$ with magnitudes equal to the induced voltages in each coil and directions defined by unit vectors vertical to the corresponding coil plane (FIG. 4A). The vectorial sum of the three vectors, denoted $\underline{Vz}$, is in the direction of the time-derivative of the local magnetic field of the Z-gradient:

(6) $\underline{Vz}=-[d(\underline{Gz}(t,x,y,z))/dt\cdot\underline{n_i}A]\underline{n_i}-[d(\underline{Gz}(t,x,y,z))/dt\cdot\underline{n_j}A]\underline{n_j}-[d(\underline{Gz}(t,x,y,z))/dt\cdot\underline{n_k}A]\underline{n_k}$ This can be easily demonstrated if we break the time derivative of the magnetic field vector ($d\underline{G}(t)/dt$) into three orthogonal components which are in the directions of three orthogonal coils. Since components parallel to the plane of each coil do not induce any voltage, the induced voltages $\underline{Vz_i}$, $\underline{Vz_j}$, $\underline{Vz_k}$ are proportional to the three components of the time derivative of the magnetic field and their sum is in the same direction as the time derivative of the magnetic field ($d\underline{G}(t)/dt$).

Finally, the magnitude of the voltage vector is proportional to the magnitude of the time-derivative of the magnetic field of the Z-gradient at the location of the coils and at the time of measurement (FIG. 4B):

(7) $|\underline{Vz}|=|(d(\underline{Gz}(t,x,y,z))/dt)A|$

The magnitudes and directions of the time-derivative of the local magnetic fields of the X and Y gradients, or of any combination of two or three magnetic fields of different gradient coils, are related (i.e. have the same direction and proportional magnitude) to the vectorial sum of the induced voltages in the three coils, as described above for the Z-gradient.

The proportionality coefficient of the relation between the magnetic field and the induced voltage in a coil is determined by the geometry of the coils, i.e. by A, the total area of the coil (if a coil with multiple loops is used the total area is the sum of all areas of the individual loops).

Figure 3A:
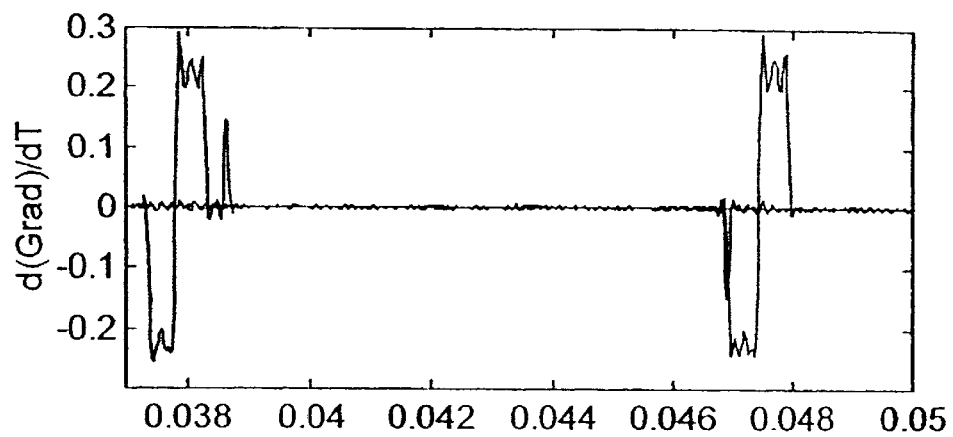
FIG. 3A presents the time-derivative of the magnetic fields of the MRI gradient coils (which are presented in FIG. 2) as functions of time.

During a typical sequence of MRI scanning two or even all three gradient coils can be activated at the same time. The magnetic fields of the gradient coils are known for a specific MRI scanner by simulation, based on the known geometry of the gradient coils, or by measurement of the fields as function of location during activation of each gradient coil. The activation sequences of each gradient coil as function of time are provided by the MRI scanner as analog signals (FIG. 2) or digital data. The known magnetic field and the activation sequence of a specific gradient coil can be used to calculate the magnetic field at each spatial location and for a specific time point, or to calculate the time derivative of the magnetic field by analog or numerical differentiation (FIG. 3A). This information can also be used to separate magnetic fields which are generated by simultaneously activated two or three gradient coils. For example, in FIG. 2 the Z-gradient coil is activated alone, while the X-gradient coil is activated alone or together with the Y-gradient coil. The magnetic and orientation of the magnetic field of the X-gradient coil can be determined from its independent activation, and this information can be used to eliminate the contribution of the magnetic field of the X-gradient coil from the induced voltages measured during simultaneous activation of the X and Y gradient coils and to extract the magnitude and orientation of the magnetic field of the Y-gradient coil.

An alternative, more general approach is to reconstruct the reference magnetic fields, which are used in the estimation process (as detailed below), as a superposition of the simultaneously activated magnetic fields of different gradients. Thus for each time point, the activation sequences of the coils are used to determine the active fields and their magnitude at the time, and the overall field is calculated by adding the field contributions from all active coils, as shown is Equations 4 and 5. The location of the device is estimated by comparing the measured voltages (during simultaneous activation of more than one gradient) to time derivative of the reference, composite magnetic field.

Step 2: Transformation from measured voltages to magnetic fields

The measured voltages are proportional to the time-derivative of the magnetic fields, and the proportionality coefficient is determined by the properties of the sensing coils (i.e. the area of each loop and the number of loops). As explained above, the time-derivative of the magnetic field is at the same direction as the voltage vector (e.g. $\underline{Vz}$ for Z-gradient) and its magnitude can be calculated by re-arranging equation (7):

(8) $|d(\underline{Gz}(t,x,y,z))/dt|=|\underline{Vz}|/A$

Figure 3B:
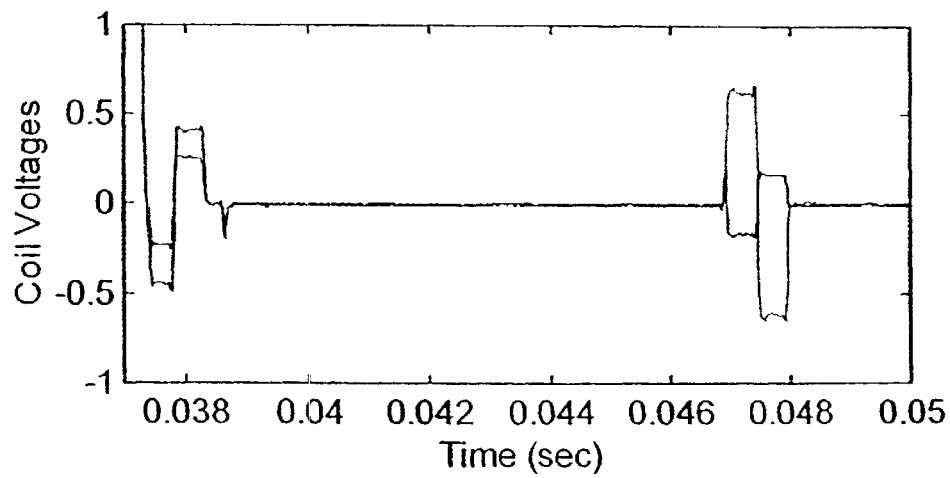
FIG. 3B presents the voltages induced by the time-varying magnetic fields of the MRI gradient coils (those presented in FIG. 2 and 3A) in two orthogonal sensing coils (e.g. 22, 24) as functions of time.

Modern MRI scanners use crushers in association with each activation of a gradient. Typically, the crushers are spike-like rapid activation and deactivation of the gradient coil. For example, in a General Electric Signa MRI scanner these crushers follow the shape of a triangle (FIG. 2) or trapezoid, and their time-derivative is similar to a positive pulse function (the up-slope of the crusher) and a negative pulse function (the down-slope of the crusher) (FIG. 3A). The induced voltages are linearly related to the time derivative of the gradient field (Equations 4 and 5) and follow the same pattern (FIG. 3B). For linear activation and de-activation of the gradients, the induced voltages during each constant phase (i.e. up-slope and down-slope) can be averaged to yield a value which is directly used to calculate the amplitude of the time-derivative of the magnetic field by equation 8. Furthermore, by measuring the time of activation or de-activation of the gradients (e.g. $\Delta t$), the amplitude of the actual magnetic field can be calculated by (for linear activation and deactivation patterns):

(9) $\underline{Gz}(t,x,y,z)=d(\underline{Gz}(t,x,y,z))/dt*\Delta t$

In the following presentation the determination of the location and orientation is based on using the magnetic field rather than their respective time-derivative. This is possible if the slope of the gradient activation pattern is linear and known, yet a similar procedure can be implemented by using the time derivative of the magnetic fields. The magnetic fields are provided by a set of 3-dimensional maps, for example by using Cartesian coordinate system with X, Y, Z coordinates. For each location, the magnetic field vector can be mapped as a set of magnitude and direction descriptors (e.g. two angles in a spherical coordinate system), or as a set of three orthogonal components of the field vector.

Step 3: Estimation of the location x,y,z of the device in the MRI coordinate system By knowing the 3-dimensional distributions of the magnetic fields of the X, Y and Z gradients (or a combination of 2 or 3 gradient fields), the instantaneous location of the device can be estimated. A search algorithm finds a specific location which, during the activation of the gradients, has magnetic fields with similar magnitudes as those calculated from the measured coil voltages. A typical search algorithm minimizes a cost function which is based on the level of similarity between the estimated fields and the reference known fields at the assumed location, for example a least squares cost function is the sum of the squares of the differences between each of the estimated magnetic fields and the corresponding reference fields at the current estimated location.

Several problems can hamper the accuracy of the estimation—the search algorithm may find a local minima of the cost function (i.e. a wrong solution), the cost function may be flat or noisy at the region of the minima which may result in a non-accurate solution, and the minimized function may have more than one solution (non-unique solution).

The problem of local minima can be solved by using search algorithms which guarantee the convergence to the true, global minima. For example, a grid search evaluates the cost function all over the potential range of solutions. For the current invention, a grid-search which evaluates the cost function at all combinations of x,y,z coordinates at a resolution of 1 cm was found to guarantee convergence to the global minima.

The accuracy of the estimation critically depends on the signal-to-noise ratio of the measurements. When only few measurements are used, for example in our case three unknown location variables are calculated from only three measurements (the amplitudes of the three voltage vectors), any noise will bias the estimation results. The effect of noise can be reduced when more measurements are used and at least-squares estimation algorithm is applied. This can be achieved by using more coils, for example a set of six coils, arranged as three orthogonal parallel pairs with known distances between the parallel coils. Obviously, more coils will generate more data with a high cost of more complex processing apparatus.

The problem of non-uniqueness of the solution is associated with multiple minima, for example due to symmetry in the cost function. The typical spatial distribution of the gradient fields in commercial MRI systems has symmetry in the three axes, and as a result up to eight equivalent minima may exist on the cost function with up to eight different solutions for the estimation process. Multiple solutions are a major limitation for any tracking method, and additional data must be used to reduce the number of solutions.

Step 4: Calculation of angles between the voltage vectors

The magnetic fields are vectors, and at each point of the imaging field the orientations of the magnetic fields of the three gradients are typically different, and can be used as additional information for the estimation process. Since the orientation of the device relatively to the MRI coordinate system is still unknown at this stage of the estimation process, the angles between the three gradient vectors are used instead of the global orientations of the vectors with respect to the MRI scanner coordinate system. The angle between any two vectors can be determined by vector algebra and analytic geometry. For example, the angle $\alpha$ between the voltage vector $\underline{Vz}$, which is induced by the Z-gradient, and the voltage vector $\underline{Vx}$, which is induced by the X-gradient, is determined by calculating the squared amplitude of the vectorial difference between the two vectors:

(10) $|\underline{Vz}-\underline{Vx}|^2=(Vz_i-Vx_i)^2+(Vz_j-Vx_j)^2+(Vz_k-Vx_k)^2$ where $Vz_i$, $Vz_j$, $Vz_k$ and $Vx_i$, $Vx_j$, $Vx_k$ are the measured voltages in the i,j,k coils during activation of the Z-gradient coil and the X-gradient coil, respectively, and then calculating the angle between the two vectors by applying the cosine law:

(11) $COS(\alpha)=(|\underline{Vz}|^2+|\underline{Vx}|^2-|\underline{Vz}-\underline{Vx}|^2)/(2*|\underline{Vz}|*|\underline{Vx}|)$ where $|\underline{Vz}|$ and $|\underline{Vx}|$ are the magnitudes of the voltage vectors induced by the Z and X gradients, respectively.

The measured angles are compared to reference angular field maps, which can be generated from the 3-dimensional field maps of the three gradients using the same approach as described by equations 10 to 11.

In the estimation process, the measured angles are compared to the reference angles at the estimated location in addition to the comparison of the magnetic fields amplitudes. This additional information improves the accuracy of the estimation process and eliminates the problem of non-uniqueness due to symmetry of the magnetic fields in the XY-plane of the MRI gradient coils.

Using the amplitudes of the voltage vectors and the angles between the vectors, there are still two equivalent anti-symmetric solutions which have the same cost-function. The gradient fields of the MRI scanner are anti-symmetric—for example for a set of values of X, Y and Z coordinates there exists a point with opposite X, Y and Z values (i.e. having the same absolute value but opposite signs) which has exactly the same absolute magnitudes and angles between the gradient field vectors. The distinction between the two anti-symmetric solutions can be done only during later stages of the estimation process, as explained below.

Following the grid search, a more accurate location can be found by local search around one of the two locations which were found to be the global minima of the cost-function. Since the two solutions are anti-symmetric, the local search can be applied around one of the two solutions and the final result can be used to find the anti-symmetric solution.

The local search applies a standard search algorithm, for example a Levenberg-Marquardt search algorithm, using either the six data points (three amplitudes of the voltage vectors and three angles, as detailed above), or with more data when it is available by using measurements from configuration with more than 3 coils.

Step 5: Determination of the device orientation

Once the spatial location of the sensor in the magnet bore is determined through steps 1–4, the X, Y, Z components of the magnetic field at this location during the operation of any gradient or gradient combination are known for a specific MRI scanner from the reference 3-dimensional magnetic field maps of the gradient coils. Using the voltages measured in each of the 3 coils during the activation of the gradients, the three rotation angles which transform from the MRI reference coordinate system to the local, device-attached coordinate system, are determined by an iterative optimization procedure. Furthermore, at this phase only one of the two anti-symmetric solutions provides a minimum of the new cost function, and a unique solution results.

An initial value of the three rotation angles is used to transform the X, Y, Z components of the magnetic fields of the three gradients into the components of the magnetic fields in the local (device) coordinate system I,J,K. According to Euler's Rotation Theorem, any spatial rotation can be described by three rotation angles, and various conventions exist for these angles. For example one convention (which is typically referred to as the Euler angles), is based on rotation around the Z axis by angle "ϕ", followed by rotation around the new X axis by angle "θ", and finally rotation around the new Y axis by angle "ψ". The three rotations can be described by a rotation matrix:

$$R = \begin{vmatrix} r_{11} & r_{12} & r_{13} \\ r_{21} & r_{22} & r_{23} \\ r_{31} & r_{32} & r_{33} \end{vmatrix} \quad (12)$$

where the rotation matrix terms are given by:
r11=cos(ψ)*cos(ϕ)−cos(θ)*sin(ϕ)*sin(ψ);
r12=cos(ψ)*sin(ϕ)+cos(θ)*cos(ϕ)*sin(ψ);
r13=sin(ψ)*sin(θ);
r21=−sin(ψ)*cos(ϕ)−cos(θ)*sin(ϕ)*cos(ψ);
r22=−sin(ψ)*sin(ϕ)+cos(θ)*cos(ϕ)*cos(ψ);
r23=cos(ψ)*sin(θ);
r31=sin(θ)*sin(ϕ);
r32=sin(θ)*cos(ϕ);
r33=cos(ψ);

Using the rotation matrix, the magnetic field vector in the reference coordinate system of the MRI scanner (i.e. in the X, Y, Z system, with components Gx, Gy, Gz) can be presented in another, rotated coordinate system. If a local coordinate system I,J,K is attached to the device, and is rotated by the three rotation angles {ϕ,θ,Ψ} in reference to the X, Y, Z system, the three Cartesian components of the magnetic field vector in the rotated system (Gi, Gj, Gk) are found by:

$$\begin{vmatrix} Gi \\ Gj \\ Gk \end{vmatrix} = \begin{vmatrix} r_{11} & r_{12} & r_{13} \\ r_{21} & r_{22} & r_{23} \\ r_{31} & r_{32} & r_{33} \end{vmatrix} \cdot \begin{vmatrix} Gx \\ Gy \\ Gz \end{vmatrix} \quad (13)$$

The calculated components of the gradient magnetic field in the I,J,K local system can be compared with the measured components in order to determine the three unknown angles of rotation. These three unknowns can be solved from the three components of one gradient field, but the results may be biased due to noise in the measurements. Better results can be achieved by using data from more gradients. Since all the three gradient fields are activated during every MRI scanning, the preferred embodiment of solving for the three angles of rotation involves the use of nine gradient field components, including 3 components for each of the 3 gradients fields (or 18 components if a set of 6 coils is used) and an optimization algorithm, for example the least squares method which is described above, to solve for the best solution.

Unlike the situation with absolute values of the measured voltages, which results with a non-unique solution composed of the true solution and an anti-symmetric one, the use of the actual measurements in each coil during the activation of each gradient or a combination of two or three gradients provides a unique solution. The gradient field components in the two locations, which corresponds to the two solutions, have the same absolute values but opposite directions, so the induced voltages in each coil have opposite signs. Although a more rigorous mathematical analysis can be used to prove the uniqueness of the solution at this phase of the estimation process, a numerical example is provided as a simple demonstration.

For a specific location (e.g. x=20.5 cm, y=10.5 cm, z=15 cm) and three rotation angles (e.g. ϕ=−40, θ80, ψ=0) the induced voltages in the three orthogonal coils during activation of a X-gradient, Y-gradient and Z-gradient are given in Table 1 (units are arbitrary and the simulation is based on maps of the gradient fields of a Signa MRI scanner). For this location, the absolute values of the voltage vectors and the angles between these vectors are calculated and given in the Table. Estimation of the location, using only amplitude of the voltage vectors, results with eight potential solutions which all have the same absolute values of the vectors. The angles between the voltage vectors are different in 6 of the 8 solutions, leaving only two equivalent solutions (the input location and the anti-symmetric solution x=−20.5 cm, y=−10.5 cm, z=−15 cm). Comparison of the components of the voltage vectors shows that they have opposing signs in the two locations, which enables the determination of the true location of the sensor.

Step 6: Improving the estimation accuracy by using measurement from all coils

Steps 1–5 described a preferred embodiment of the invention using a two-tier estimation process, the first one determines the location and the second one determines the orientation of the object or the device, when only three orthogonal coils are used or when the measurements from the two coils in each pair are simply averaged. However, when all the measurements are used in the estimation process a more accurate estimation result can be achieved.

The estimation process aims to find the 6 unknowns which fully define the spatial location and orientation of the sensor. Since the exact distance between the two coils of each pair is accurately known, the estimation process still aims to find 6 unknowns, for example the location and orientation of a set of three orthogonal coils, while the location and orientation of the second set of the three orthogonal coils can be defined with respect to the location and orientation of the first set. Thus, although we get more measurements (18 voltages for the 6 coil during operation of each of the three MRI gradient coils) we still have the same number of unknowns. A larger amount of data for the estimation process is a key for more accurate solution of the optimization process.

The effect of voltages induced by the Bo field when the sensor moves or rotates

Equation 4 provides the general description for the induced voltages in the sensor coils, but the description above assumes no effect of the Bo field. This assumption is correct as long as the sensor does not move, or when the movements are relatively slow. Since the typical rise time of gradients in modern MRI system is 1 millisecond (FIG. 2), and body or device movements are typically slower (in scale of seconds or tenth of a second), the effect of the Bo can be eliminated by appropriate high pass filtering of the signals from the sensor coils (for example a 100 Hz cut-off frequency), and the description above can be applied on the filtered signals during movements and rotations of the body organs (e.g. the head) or the device.

Yet the voltages induced in the sensor coils by the Bo magnetic field can be advantageously used to improve the tracking of the location and the orientation of the device or the object. Unlike the gradient fields which change in time, the Bo is constant and it induces electric potential in the sensor coils only when there is rotation of the coils which change the magnetic flux through the coils. Unlike equation 3 above, the time varying variable now is the direction of the coils which is given by a time variable unit vector n(t):

(14) $\Theta = \underline{G} \cdot \underline{n}(t) A$

By applying low-pass filter on the sensor signals the Bio-induced voltages can be extracted and used to estimate the time change of the sensor orientation, i.e. the three angular velocities of the device or the sensor. This information can be used to improve the estimation process based on the magnetic fields of the gradients (e.g. by providing a better initial guess to the iterative estimation processes) or to enable better prediction of future location and orientation of the device or the sensor.

Preferred Embodiment of the Sensor

Figure 5A:
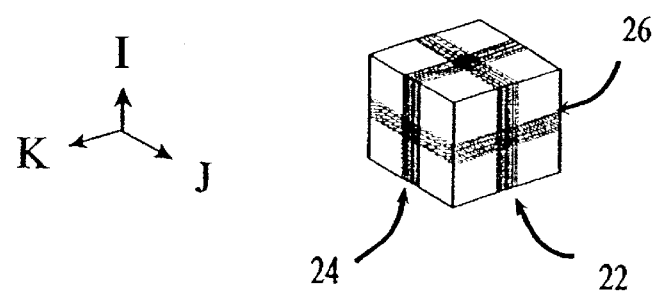
FIGS. 5A–5D illustrate three potential configurations of coils which provide a set of three orthogonal coils or pairs of coils.

The preferred, minimal configuration of the sensor includes three coils. The disclosed invention covers also a lesser configuration of two coils, using the same approach as presented above, and using the 6 potentials induced by the three MRI gradients in the two coils to calculate the 6 unknowns (3 locations and 3 rotations angles). However, for optimal performance more data should be used to reduce the effects of noise and to improve the accuracy of the tracking. A potential configuration with three orthogonal coils is presented in FIG. 5A. This configuration is suitable for extra-corporeal applications, for example devices for minimal invasive procedures like biopsy guns or surgery instruments. Furthermore, the inner space of the sensor can be used to contain electronic circuitry, powered by a miniature battery, for signal conditioning (e.g. filtration and amplification), signal transformation (e.g.into optical signal, or into frequency modulated (FM) signal), or for wireless transmission of the measured potentials.

Figure 5B:
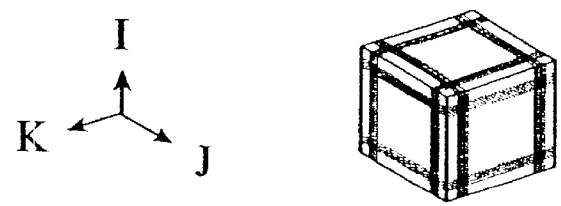

A more complex configuration is presented in FIG. 5B, where three pairs of parallel coils can be used instead of three single coils, e.g., a total of 6 coils is used in a sensor. The major advantage of this configuration is a substantial increase in the accuracy of the tracking, since for each activation of any MRI gradient, six, rather than three, different potentials are induced, and a total of 18 measurements is available to estimate the 3 unknown location variables and the 3 unknown rotation angles with each cycle of scanning. Although the distance between each of the two parallel coils is small (e.g. 5–10 mm in the cubic configuration of FIG. 5A and 1–2 mm in the cylindrical configuration of FIG. 5C and 5D), the steep gradients used with modem MRI scanners on one hand, and the availability of the exact distance between the two parallel coils on the other hand, enable the use of this information to increase the accuracy of the tracking.

Figure 5C:
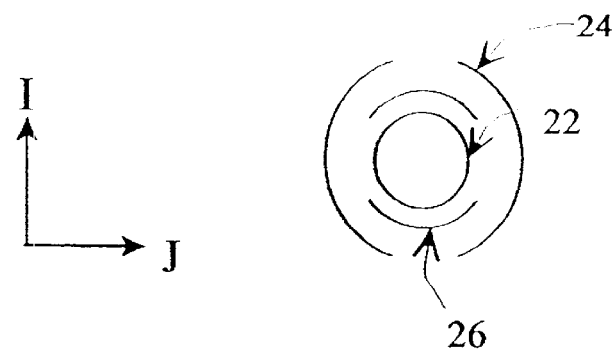
Figure 5D:
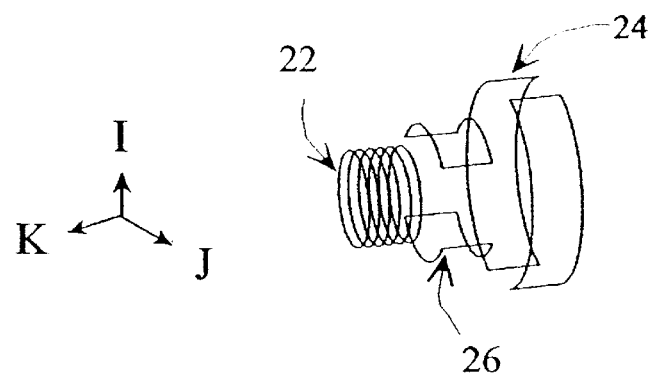

A second preferred configuration is presented in FIGS. 5C and D, and includes a cylindrical coil and two pairs of "saddle" coils positioned in orthogonal directions to the cylindrical coils and to each other (FIG. 5C presents an axial view of the set of coils and FIG. 5D presents an isometric view of the two pairs of saddle coils and an inner cylindrical coils, all three coils are axially displaced to clarify the presentation). This configuration is specifically useful for catheters tracking since it has a hollow cylindrical structure and it can be fixed on the tip of any catheter without blocking the lumen of the catheter. It can be used with stent placement apparatus, with various diagnostic catheters (e.g. for intracardiac electrophysiology studies) and with current or future therapeutic catheters (e.g. RF ablation, laser ablation, percutaneous transmyocardial revascularization (PMR), targeted drug delivery, local genetic substance placement, etc.).

In a variant of the cylindrical hollow configuration the two pairs of "saddle" coils are replaced by two planar coils, which may be positioned inside or outside the lumen of the cylindrical coil. Although this configuration partially blocks the catheter lumen, it is simpler to manufacture and may be useful with applications which do not require free lumen.

The sensors can be assembled from individual coils, for example by glueing 6 small flat coils on the 6 surfaces of a cube. On a catheter, one pair of coils has a cylindrical shape and can be directly wired over the shaft of the catheter, while the two other pairs have saddle shape, and can be glued around the cylindrical coils. Another potential approach for the construction of the multi-coil sensor is by using flexible printed electrical circuits, which include all the coils and are folded to achieve the 3-dimensional shape.

Preferred Embodiment of the Tracking Apparatus

Figure 6:
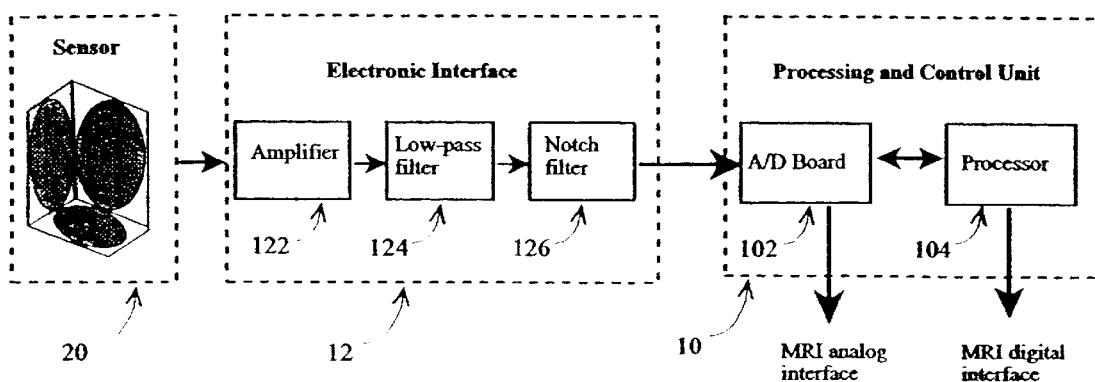
FIG. 6 presents a block diagram of the measurement and processing system, including the sensor (20), the electronic interface (12) and the processing and control unit (10).

The tracking apparatus (FIG. 6) includes the sensor 20, the electronic interface 12, the processing module 10, and the interface with the MRI scanner. It can be customdesigned and built for the specific tracking application or assembled from commercially available components.

The electronic interface (12) contains a set of amplifiers (122) to amplify the low-voltage potentials which are induced in the coils (from millivolts level to volts), a set of low-pass filters (124) to eliminate the high frequency voltage which are induced by the RF transmission, having frequency range of 10–400 MHz (depending on the MRI magnet strength), and stop-band or notch filter (126) to remove potentials induced by the step-wise increase of the MRI gradients, which in a General Electric MRI scanner produce a 128KHz artifact. Various commercial systems with programmable amplified/filter combinations can be used to amplify and filter the low-voltage signals from the sensors (e.g. SCS-802, Alligator Technologies, Costa-Mest, Calif.).

The processing and control unit (10) can be developed using readily available commercial hardware. For example, the measured signals from the sensor can be digitized by analog-to-digital (A/D) converter (102) using a standard data acquisition board (e.g. National Instruments, Austin, Tex.), and processed in real-time by a modern, high performance processor 104 (e.g. a Pentium III processor with MMX built-in DSP). Another potential solution, which provides faster estimation rates, can be based on digital signal processor (DSP) boards, having built-in or attached A/D converter having at least 6 channels (3 coil signals and 3 MRI gradient signals), high-performance DSP for iterative solution of location and orientation, sufficient memory capacity for the program and for data (e.g. the reference magnetic fields), and communication bus for interface with the host computer or directly with the MRI scanner (e.g. Blacktip-CPCI processing board and BITSI-DAQ analog input/output adapter, Bittware Research Systems, Concord, N.H.). The software for the DSP or the PC processor can be developed with standard programming languages, for example C++ or assembly. We have used the Matlab software development environment (The Math Works, Natick, Mass.) to rapidly implement the estimation process as described above.

The interface with the MRI includes two main components—a channel to transfer the real-time location and orientation of the sensor, and a channel (or channels) to transfer the activation pattern of the gradient coils from the MRI scanner to the processing module. Either digital communication channel, analog channels, or a combination of the two can be used. With the Signa MRI system, for example, the gradient activation sequence is available as standard analog output from the gradient control system, and tracking information can be received by the MRI through a standard serial communication line.

Figure 7:
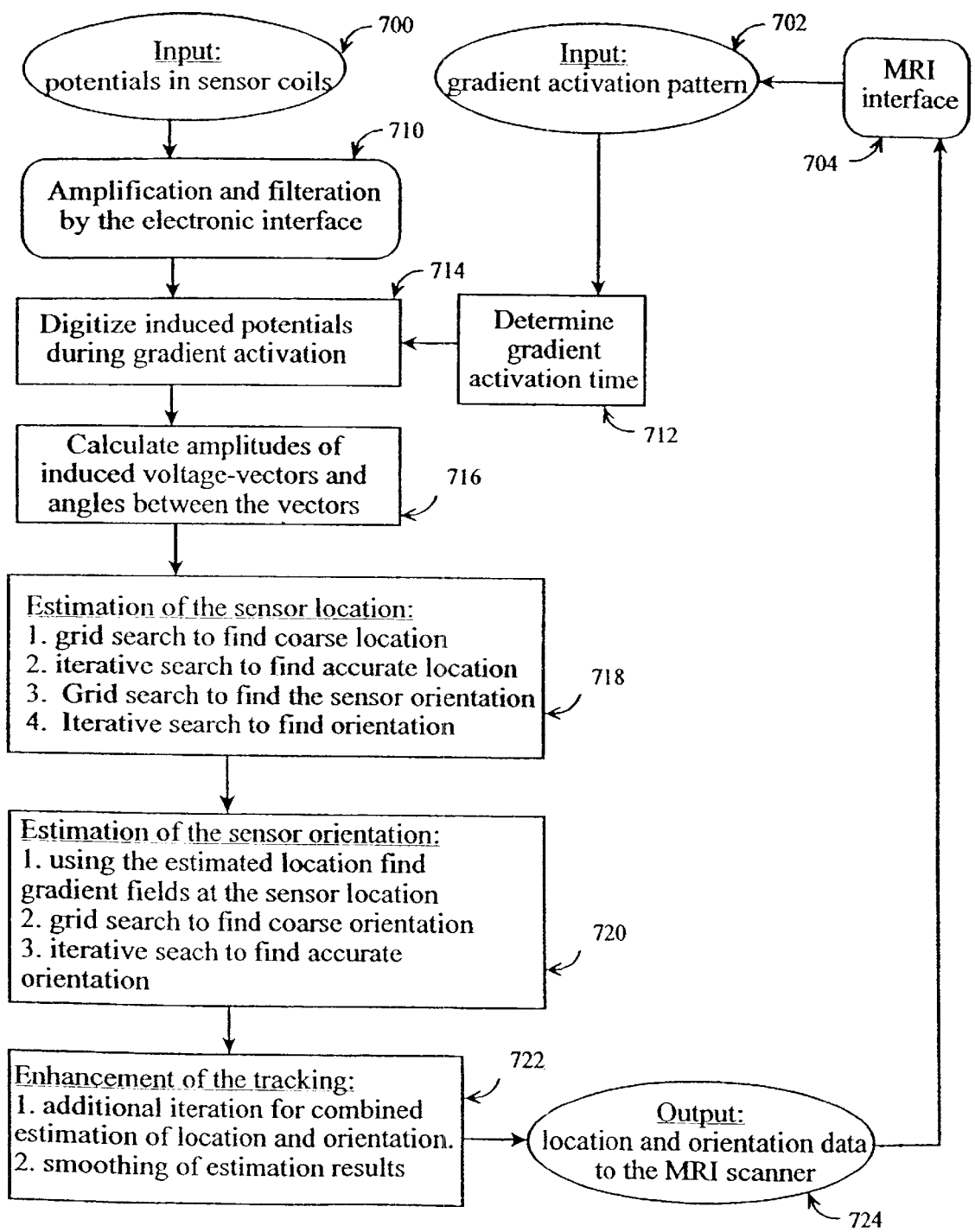
FIG. 7 presents a block diagram of the preferred embodiment of the tracking methodology for various clinical uses.

The overall operation of the tracking system is presented below and in FIG. 7. The induced potentials in the sensors (700), typically having a magnitude of millivolts, are amplified and filtered by the electronic interface module (710). The activation pattern from the MRI scanner (702) is transferred to the tracking system through the MRI interface module (704) and may be processed by the electronic interface module (e.g. filtered) before it is digitized by the processing module. The activation pattern of the MRI gradients (FIG. 2) is analyzed by the processor to determine the activation of each of the gradient coils, e.g. by threshold triggering (712). Typically we will use the crushers which have longer activation times and higher amplitude of magnetic fields. Once an activation of any gradient coil is detected, the processor digitizes the signal from the coils and process it to determine the level of the induced signals (714). If the activation of the gradient is linear, its time-derivative during the activation is flat (FIG. 3A) and the induced potential in the sensor coils is also flat (FIG. 3B). Thus, the measured signals can be averaged as long as the gradient activation is on. It should be noted, however, that non-linear activation patterns can be used as long as a description of the activation pattern of the gradient coils is available. The measured signals from the three orthogonal coils are calibrated into magnetic fields units using the calibration factors of the coils (Equations 8 and 9). The measured induced voltages in the set of orthogonal coils are used to calculate the amplitude of the voltage-vector (Equations 6–7) and the angles between the voltage-vectors of the different MRI gradients (Equations 10–11) (716). These amplitudes and angles are used to estimate the location of the sensor in the MRI coordinate system (block 718, 3) and to estimate the orientation of the sensor (block 720, 4). The estimated location and orientation may be further processed to improve the quality of the tracking, e.g. by the application of a low-pass digital filter on the estimations at a specific time, using previous estimations, and may be transformed into a data format which is required by the MRI scanner (722). Finally, the tracking data (724) is transferred to the MRI scanner through the MRI interface module (704).

Clinical Applications

The determined location and orientation of the sensor can be transferred to the MRI scanner in real-time and used for various tasks, for example for real-time control of the scanning plane, to display the location and orientation of the object or the device with the tracking sensor on the MR image, to correct motion artifacts. Potential clinical applications of the invention can be divided into applications for diagnostic MR imaging and for interventional MRI.

Diagnostic MRI: A major problem with MR imaging is motion artifacts due to patient movement. With high-resolution scanning, which may require image acquisition during many seconds and even minutes, patient movement and breathing may induce motion artifacts and blurred images. MR scanning is specifically sensitive to movements during phase contrast angiography, diffusion imaging, and functional MRI with echo-planar imaging (EPI). Using the present invention for real-time determination of the location and orientation of the scanned object can reduce the effect of motion on the MR scans by real-time control and correction of the scanning plane, in order to compensate for the movement, or by post-acquisition image processing.

Interventional MRI: The sensor can be used with various devices, like miniature tools for minimally invasive surgery, catheters inside blood vessels, rigid and flexible endoscopes, biopsy and aspiration needles. It can be used to measure the location of the device with respect to the MRI coordinate system and to enable the MR scanner to present the device location on the MR images, as visual feedback to the operator, or to calculate and display the line of current orientation to assist the operation to steer the device into a specific target. Another potential application is to slave the MRI plane of imaging to the tracking sensor, for example to apply high resolution imaging on a small volume around the site of a catheter, for better imaging of the region of interest to improve diagnostic performance or to control the effect of an intervention (e.g. radio-frequency, cryo, or chemical ablation and laser photocoagulation can be monitored by temperature-sensitive MR imaging). Another potential application is to use the information of the location and orientation of the device in order to enable display of the MRI images in reference to the device local coordinate system, as if the operator is looking through the device and in the direction of the tip, similar to the use of optical endoscopes. One more application is to use the location tracking in order to mark location of previous interventions on the MRI image.

An application with great clinical importance, where using MRI guidance is of specific advantage, is percutaneous myocardial revascularization (PMR). PMR is typically performed during cardiac catheterization. A laser transmitting catheter is inserted through the femoral artery up through the aorta into the left ventricle of the heart. Based on prior perfusion studies (e.g. Thallium scan) or indirect information on viability of the myocardium (e.g. by measurement of local wall motion), the cardiologist applies laser energy to drill miniature channels in the inner portion of the heart muscle, which stimulates angiogenesis and new blood vessel growth. PMR potentially provides a less invasive solution (compared to bypass surgery) for ischemic heart disease patients which cannot be adequately managed by angioplasty or stent placement. It may also be used in conjunction with angioplasty or stent to treat areas of the heart not completely revascularized by a balloon or stent placement. Currently, PMR is exclusively done with X-ray guidance. The main advantage of MRI is the excellent performance of MRI in the assessment of myocardial blood perfusion, through the use of contrast agents. Thus rather than using indirect information on the location of poorly perfused regions, a diagnostic session of myocardial perfusion in the MRI scanner can be followed by immediate intervention, using the existing perfusion images and real-time tracking of the laser catheter with the disclosed tracking methodology. Additional advantage, unique to MRI, is the potential to control the intervention by high-resolution, real-time imaging of the myocardium during the application of the laser treatment. Furthermore, since PMR is typically performed on multiple locations, and a good coverage of the treated myocardium should be achieved, marking the location of the treated locations on the perfusion image, using the location data of the tracking system, may provide optimal coverage of the diseased region.

Anatomically, the tracking sensor can be used for various diagnostic and interventional procedures inside the brain (internally through blood vessels or through burr holes in the scull), the cardiovascular system (heart chambers, coronary arteries, blood vessels), the gastro-intestinal tract (stomach, duodenum, biliary tract, gall bladder, intestine, colon) and the liver, the urinary system (bladder, ureters, kidneys), the pulmonary system (the bronchial tree or blood vessels), the skeletal system (joints), the reproductive tract, and others.

TABLE 1

Induced voltages in 3 orthogonal coils were simulated for a sample location (X = 20.5 cm, Y = 10.5 cm, Z = 15.0 cm) inside an MRI scanner during the activation of three gradients and are presented in the lower section of the table as voltage vectors (Vx, Vy, Vz). Using only the absolute amplitudes of the voltage vectors (|Vx|, |Vy|, |Vz|) results with eight different solutions (Xest, Yest, Zest). The use of the angles between the voltage vectors (XZ_ang, YZ_ang, YX_ang) eliminates 6 of the solutions and provides two anti-symmetric equivalent solutions (1 and 8). Finally, when the three components of each of the three voltage vectors are used (Vx, Vy, Vz), a unique correct solution (solution 8) is obtained.

|  | Solution 1 | Solution 2 | Solution 3 | Solution 4 | Solution 5 | Solution 6 | Solution 7 | Solution 8 |
|---|---|---|---|---|---|---|---|---|
| Xest | −20.50 | 20.50 | −20.50 | 20.50 | −20.50 | 20.50 | −20.50 | 20.50 |
| Yest | −10.50 | −10.50 | 10.50 | 10.50 | −10.50 | −10.50 | 10.50 | 10.50 |
| Zest | −15.00 | −15.00 | −15.00 | −15.00 | 15.00 | 15.00 | 15.00 | 15.00 |
| |Vx| | 27.7918 | 27.7918 | 27.7918 | 27.7918 | 27.7918 | 27.7918 | 27.7918 | 27.7918 |
| |Vy| | 19.6513 | 19.6513 | 19.6513 | 19.6513 | 19.6513 | 19.6513 | 19.6513 | 19.6513 |
| |Vz| | 19.8370 | 19.8370 | 19.8370 | 19.8370 | 19.8370 | 19.8370 | 19.8370 | 19.8370 |
| XZ ang | 9.7436 | −7.6928 | 7.6928 | −9.7436 | −9.7436 | 7.6928 | −7.6928 | 9.7436 |
| YZ ang | −11.1176 | −5.3237 | 5.3237 | 11.1176 | 11.1176 | 5.3237 | −5.3237 | −11.1176 |
| YX ang | −13.0904 | 26.7508 | 26.7508 | −13.0904 | −13.0904 | 26.7508 | 26.7508 | −13.0904 |
| Vx | −16.2143 | −16.2143 | −16.2143 | −16.2143 | 16.2143 | 16.2143 | 16.2143 | 16.2143 |
|  | −21.2103 | 17.2907 | −21.2103 | 17.2907 | −17.2907 | 21.2103 | −17.2907 | 21.2103 |
|  | 7.7202 | 14.5090 | 7.7202 | 14.5090 | −14.5090 | −7.7202 | −14.5090 | −7.7202 |
| Vy | −12.2805 | −12.2805 | −12.2805 | −12.2805 | 12.2805 | 12.2805 | 12.2805 | 12.2805 |
|  | 11.6284 | 11.6284 | −7.5044 | −7.5044 | 7.5044 | 7.5044 | −11.6284 | −11.6284 |
|  | −10.0072 | −10.0072 | −13.3808 | −13.3808 | 13.3808 | 13.3808 | 10.0072 | 10.0072 |
| Vz | 4.9383 | −12.0771 | 12.0771 | −4.9383 | 4.9383 | −12.0771 | 12.0771 | 4.9383 |
|  | −13.2568 | −15.7361 | −14.7342 | −17.2135 | 17.2135 | 14.7342 | 15.7361 | 13.2568 |
|  | −13.9060 | 0.1548 | −5.5275 | 8.5332 | −8.5332 | 5.5275 | −0.1548 | 13.9060 |

What is claimed is:

1. A method of determining the instantaneous location and orientation of an object moving through a three-dimensional space within the imaging space of magnetic resonance imaging apparatus during operation of said magnetic resonance imaging apparatus, comprising:

applying to said object a sensor that measure instantaneous magnetic field within said imaging space of magnetic resonance imaging apparatus;

measuring the instantaneous values of the magnetic fields which are generated by the activation of the gradient coils of said magnetic resonance imaging apparatus during operation of said magnetic resonance imaging apparatus; and processing said measured instantaneous values of the magnetic fields, together with the known magnitude and direction of said magnetic fields of said gradient coils, to compute the instantaneous location and orientation of said object within said space.

2. The method according to claim 1, wherein said sensor comprises a coil assembly including a plurality of sensor coils having axes of known orientation with respect to each other and including components in the three orthogonal planes.

3. The method of claim 2, wherein said step of measuring further includes the step of identifying a plurality of activations of the magnetic gradient fields of said magnetic resonance imaging apparatus, wherein said identification provides the timing and the amplitude of activations of a single gradient coil or combined activations of two or three gradient coils of said magnetic resonance imaging apparatus; and wherein said step of processing further comprises:

i. calculating voltage vectors by vectorial summation of induced electrical potentials in different sensor coils for each said activation of the gradient fields of the MRI scanner;

ii. calculating the magnitudes of all said voltage vectors and the angles between all possible pairs of said voltage vectors;

iii. storing in memory the reference magnetic field maps of each of the three gradient coils of said magnetic resonance imaging apparatus for the imaging space of said magnetic resonance imaging apparatus;

iv. estimating the location of the sensor by processing said calculated magnitudes and angles of said voltage vectors together with the known reference magnetic field maps and the known relative orientation of the sensor coils in said coils assembly; and v. estimating the orientation of the sensor by processing said induced electrical potentials generated in said sensor coils together with the known reference magnetic field maps and the known relative orientation of the sensor coils in said coil assembly.

4. The method of claim 2, wherein said step of measuring further includes identifying a plurality of activations of the magnetic gradient fields of said magnetic resonance imaging apparatus, wherein said identification provides the timing and the amplitude of activations of a single gradient coil or combined activations of two or three gradient coils of said magnetic resonance imaging apparatus; and wherein said step of processing further comprises:

i. storing in memory the reference magnetic field maps of each of the three gradient coils of said magnetic resonance imaging apparatus for the imaging space of said magnetic resonance imaging apparatus; and ii. simultaneously estimating the location and the orientation of the sensor by processing said induced electrical potentials generated in said sensor coils together with the known reference magnetic field maps and the known relative orientation of the sensor coils in said coil assembly.

5. The method according to claim 2, wherein said coil assembly includes at least three sensor coils oriented orthogonally with respect to each other.

6. The method according to claim 2, wherein said coil assembly includes three pairs of sensor coils, in which one sensor coil in each pair has the same orientation as the other sensor coil in the respective pair, and in which each pair of sensor coils has a different orientation from the other pairs of sensor coils.

7. The method according to claim 6, wherein each sensor coils in a pair is parallel to, but laterally spaced from, the other sensor coil of the pair.

8. The method according to claim 2, wherein said coil assembly includes a cylindrical sensor coil and two pairs of sensor coils positioned orthogonally with respect to the cylindrical sensor coil.

9. The method according to claim 8, wherein said two pairs of sensor coils are curved and in a saddle relation to said cylindrical sensor coil.

10. The method according to claim 8, wherein said two pairs of sensor coils are planar.

11. The method according to claim 1, wherein said processing is effected by an iterative optimization process.

12. The method according to claim 11, wherein said iterative optimization process is effected in real time to determine the instantaneous location and orientation of said object in real time.

13. The method according to claim 1, wherein said object is a medical instrument moving in the body of a person for medical diagnostic or treatment purposes.

14. The method according to claim 13, wherein said medical instrument is selected from the group consisting of: a catheter for arteriogram, a catheter for venogram, a catheter for angioplasty, a catheter for stent placement, a catheter for percutaneous transmyocardial revascularization, a catheter for cardiac electrophysiology studies, and a catheter for gene therapy.

15. The method according to claim 13, wherein said medical instrument is a tool for minimal invasive surgery.

16. The method according to claim 13, wherein said medical instrument is selected from the group consisting of: a biopsy gun, a biopsy needle, and an aspiration needle.

17. The method according to claim 13, wherein said medical instrument is selected from the group consisting of: a rigid endoscope, a flexible endoscope, a ventriculoscope, a colonoscope, a duodenoscope, a gastroscope, a laryngoscope, a tracheoscope, a bronchoscope, a hysteroscope, an urethroscope, a cystoscope, an ureteroscope, and an arthroscope.

18. The method according to claim 1, wherein said object is a motion sensor.

19. Apparatus for determining the instantaneous location and orientation of an object moving through a three-dimensional space within the imaging space of magnetic resonance imaging apparatus during operation of said magnetic resonance imaging apparatus, comprising:
   a sensor carried by said object that measures instantaneous magnetic field within said imaging space of magnetic resonance imaging apparatus;
   means for measuring the instantaneous values of the magnetic fields which are generated by the activation of the gradient coils of said magnetic resonance imaging apparatus during operation of said magnetic resonance imaging apparatus; and
   a processor for processing said measured instantaneous values of said magnetic fields, together with the known magnitude and direction of said magnetic fields of said gradient coils, to compute the instantaneous location and orientation of said object within said space.

20. The apparatus according to claim 19, wherein said sensor comprises a coil assembly including a plurality of sensor coils having axes of known orientation with respect to each other and including components in the three orthogonal planes.

21. The apparatus of claim 20, wherein said measuring means further includes the means for identifying a plurality of activations of the magnetic gradient fields of said magnetic resonance imaging apparatus, wherein said identification provides the timing and the amplitude of activations of a single gradient coil or combined activations of two or three gradient coils of said magnetic resonance imaging apparatus; and
   wherein said processor further comprises:
      i. means for calculating voltage vectors by vectorial summation of induced electrical potentials in different sensor coils for each said activation of the gradient fields of the MRI scanner;
      ii. means for calculating the magnitudes of all said voltages vectors and the angles between all possible pairs of said voltages vectors;
      iii. memory for storing in reference magnetic field maps of each of the three gradient coils of said magnetic resonance imaging apparatus for the imaging space of said magnetic resonance imaging apparatus;
      iv. means for estimating the location of the sensor by processing said calculated magnitudes and angles of said voltage vectors together with the known reference magnetic field maps and the known relative orientation of the sensor coils in said coil assembly; and
      v. means for estimating the orientation of the sensor by processing said induced electrical potentials generated in said sensor coils together with the known reference magnetic field maps and the known relative orientation of the sensor coils in said coil assembly.

22. The apparatus of claim 20, wherein said measuring means further comprises means for identifying a plurality of activations of the magnetic gradient fields of said magnetic resonance imaging apparatus, wherein said identification provides the timing and the amplitude of activations of a single gradient coil or combined activations of two or three gradient coils of said magnetic resonance imaging apparatus; and
   wherein said processor further comprises:
      i. memory for storing the reference magnetic field maps of each of the three gradient coils of said magnetic resonance imaging apparatus for the imaging space of said magnetic resonance imaging apparatus; and
      ii. means for simultaneously estimating the location and the orientation of the sensor by processing said induced electrical potentials generated in said sensor coils together with the known reference magnetic field maps and the known relative orientation of the sensor coils in said coil assembly.

23. The apparatus according to claim 20, wherein said coil assembly includes at least three sensor coils oriented orthogonally with respect to each other.

24. The apparatus according to claim 20, wherein said coil assembly includes three pairs of sensor coils, in which one sensor coil in each pair has the same orientation as the other sensor coil in the respective pair, and in which each pair of sensor coils has a different orientation from the other pairs of sensor coils.

25. The apparatus according to claim 20, wherein each sensor coil in a pair is parallel to, but laterally spaced from, the other sensor coil of the pair.

26. The apparatus according to claim 20, wherein said coil assembly includes a cylindrical sensor coil and two pairs of sensor coils positioned orthogonally with respect to the cylindrical sensor coil.

27. The apparatus according to claim 26, wherein said two pairs of sensor coils are curved and in a saddle relation to said cylindrical sensor coil.

28. The apparatus according to claim 26, wherein said two pairs of sensor coils are planar.

29. The apparatus according to claim 19, wherein said processor effects an iterative optimization process.

30. The apparatus according to claim 29, wherein said iterative optimization process is effected in real time to determine the instantaneous location and orientation of said object in real time.

31. The apparatus according to claim 19, wherein said object is a medical instrument moving in the body of a person for medical diagnostic or treatment purposes, and wherein said sensor is adhered to, or integrated into, said medical instrument.

32. The apparatus according to claim 31, wherein said medical instrument is selected from the group consisting of: a catheter for arteriogram, a catheter for venogram, a catheter for angioplasty, a catheter for stent placement, a catheter for percutaneous transmyocardial revascularization, a catheter for cardiac electrophysiology studies, and a catheter for gene therapy.

33. The apparatus according to claim 31, wherein said medical instrument is a tool for minimal invasive surgery.

34. The apparatus according to claim 31, wherein said medical instrument is selected from the group consisting of: a biopsy gun, a biopsy needle, and an aspiration needle.

35. The apparatus according to claim 31, wherein said medical instrument is selected from the group consisting of: a rigid endoscope, a flexible endoscope, a ventriculoscope, a colonoscope, a duodenoscope, a gastroscope, a laryngoscope, a tracheoscope, a bronchoscope, a hysteroscope, an urethroscope, a cystoscope, an ureteroscope, and an arthrocope.

36. The apparatus according to claim 19, wherein said object is a motion sensor.

* * * * *